(12) United States Patent
Ren et al.

(10) Patent No.: US 8,357,796 B2
(45) Date of Patent: Jan. 22, 2013

(54) PGG SEPARATION AND PURIFICATION

(75) Inventors: Yulin Ren, Athens, OH (US); Klaus B. Himmeldirk, Vincent, OH (US); Xiaozhou Chen, Athens, OH (US)

(73) Assignee: Ohio University, Athens, OH (US)

( * ) Notice: Subject to any disclaimer, the term of this patent is extended or adjusted under 35 U.S.C. 154(b) by 1231 days.

(21) Appl. No.: 10/597,395

(22) PCT Filed: Jan. 24, 2005

(86) PCT No.: PCT/US2005/002262
§ 371 (c)(1),
(2), (4) Date: Jul. 24, 2006

(87) PCT Pub. No.: WO2005/070943
PCT Pub. Date: Aug. 4, 2005

(65) Prior Publication Data
US 2008/0249299 A1    Oct. 9, 2008

Related U.S. Application Data

(60) Provisional application No. 60/538,698, filed on Jan. 23, 2004.

(51) Int. Cl.
*C07H 1/06* (2006.01)
(52) U.S. Cl. ...................................... 536/127
(58) Field of Classification Search .................. 536/127
See application file for complete search history.

(56) References Cited

U.S. PATENT DOCUMENTS

| 4,107,425 | A * | 8/1978 | Pfeffer et al. .................. 536/119 |
| 7,687,472 | B2 | 3/2010 | Chen et al. |
| 7,772,381 | B2 | 8/2010 | Himmeldirk et al. |
| 7,888,042 | B2 | 2/2011 | Chen |
| 2004/0258773 | A1 | 12/2004 | Chen et al. |
| 2006/0058243 | A1 | 3/2006 | Chen et al. |

FOREIGN PATENT DOCUMENTS

| WO | 98/42350 A1 | 10/1998 |
| WO | 2004/009094 A1 | 1/2004 |
| WO | 2005/072765 A2 | 8/2005 |
| WO | 2006/034468 A2 | 3/2006 |

OTHER PUBLICATIONS

Ault, A., Techniques and Experiments for Organic Chemistry, 1987, 44-46.*
Merriam Webster OnLine Dictionary, p. 1.*
Khanbabaee er al, Tetrahedron, 1997, 53(1), 10725-32.*
Experimental Organic Reactions, 1957, 18, pp. 504-505, English Translation.*
Farag et al, Bull. Pharm. Sci. Assiut University, 1998, 21(1), 1-6.*
Ault, A., Techniques and Experiments for Organic Chemistry, 1987, pp. 120-121.*
Feldman et al, Phytochemistry, 1999, 51, 867-72.*
Written Opinion for PCT/US05/02262, dated Jun. 20, 2005.
International Search Report for PCT/US05/02262, dated Jun. 20, 2005.
Leonard et al., Chapter 11—Purification, Advanced Practical Organic Chemistry, 2nd Ed., 2001 reprint, Nelson Thornes, Ltd., Cheltenham, United Kingdom, pp. 184-226.

\* cited by examiner

*Primary Examiner* — Shaojia Anna Jiang
*Assistant Examiner* — Ganapathy Krishnan
(74) *Attorney, Agent, or Firm* — Calfee, Halter & Griswold LLP

(57) ABSTRACT

A simple, inexpensive, and efficient method for separation and purification of the α- and β-forms of penta-O-galloyl-D-glucose (PGG) without the need for HPLC. The methods provided herein are useful for separation α-PGG or β-PGG from a mixture containing α-PGG and β-PGG and other chemicals. The method for separation of α-PGG from a mixture of α-PGG and β-PGG comprises the steps of: adding water to a sample containing 50% or more α-PGG and 50% or less β-PGG; mixing the PGG and water to dissolve the PGG; filtering out any undissolved particles; and allowing the filtered solution to stand undisturbed until crystals form.

23 Claims, 1 Drawing Sheet

β-PGG crystals (x 50)
Short and rod-like
α-PGG crystals (x 50)
Long, thin and needle-like

PGG SEPARATION AND PURIFICATION

CROSS-REFERENCE TO RELATED APPLICATION

This application claims priority to U.S. Provisional Application No. 60/538,698 filed Jan. 23, 2004, the entirety of which is incorporated herein by reference.

BACKGROUND OF THE INVENTION

PGG and its analogues show anti-diabetic and other beneficial bioactivities that make them useful in the development of new drugs. Typically, for FDA approval of new drugs, the purity of the drugs must be higher than 95%. Currently, there are no efficient, cost-effective methods of preparing and purifying PGG or its analogues on a gram to kilogram scale. Until now, chromatographic purification methods have been the only known methods for producing PGG or its analogues at a purity of 95% or greater. Chromatographic methods, however, are both expensive and not amenable to large scale purification of PGG and its analogues. Production of PGG on an industrial scale using currently available methods is prohibitively expensive.

Accordingly, there exists a need for methods of separation and purification of PGG and its analogues that are less expensive than currently known methods, and amenable to larger scale production.

SUMMARY OF THE INVENTION

) Provided herein is a simple, inexpensive, and efficient method for separation and purification of the $\alpha$- and $\beta$- forms of penta-O-galloyl-D-glucose (PGG). Specifically, the methods provided herein are useful for separating $\alpha$-PGG or $\beta$-PGG from a mixture that contains $\alpha$-PGG and $\beta$-PGG and other chemicals. The methods described herein, unlike previous separation and purification methods, require no HPLC step. Because no HPLC step is required, the methods described herein, are amenable to producing large quantities of purified $\alpha$-PGG and $\beta$-PGG.

Provided is a method of separating $\alpha$-PGG from a mixture containing $\alpha$-PGG and $\beta$-PGG. Also provided is a method for separating $\beta$-PGG from a mixture containing both $\alpha$-PGG and $\beta$-PGG. The methods described herein are especially suitable for separating $\alpha$-PGG from a mixture of $\alpha$-PGG and $\beta$-PGG that contains more than 50% $\alpha$-PGG, or separating $\beta$-PGG from a mixture of $\alpha$-PGG and $\beta$-PGG that contains more than 50% $\beta$-PGG.

Also provided are methods of purifying $\alpha$-PGG and $\beta$-PGG to purities of greater than 95%. In one embodiment, the method provides $\alpha$-PGG or $\beta$-PGG at greater than 98% purity. Also provided are methods of growing single crystals of $\alpha$-PGG and single crystals of $\beta$-PGG.

Also provided are methods for the separation and purification of analogues of $\alpha$- and $\beta$-PGG in which the glucose part of the PGG is substituted by other sugars. In some embodiments, the sugars are hexoses, pentoses, or tetroses. In embodiments where the glucose is substituted with one or more hexoses, the hexoses may be selected from, but not limited to galactose, mannose, idose, talose, altrose, allose, gulose, fructose, or similar. In embodiments wherein the glucose is replaced by one or more pentoses, the pentoses may be selected from, though are not limited to, xylose, ribose, arabinose, and lyxose. In embodiments wherein the glucose is replaced with a tetrose, suitable tetroses include, but are not limited to threose and erythrose. The methods described herein are able to separate the $\alpha$- and $\beta$-PGG analogues from mixtures containing both the $\alpha$-form and the $\beta$-form. In accordance with the methods described herein the $\alpha$-form of the analogue is separated from mixtures that containing 50% or more of the $\alpha$-fonm; and the $\beta$-form of the analogue is separated from mixtures that contain 50% or more of the $\beta$-form. In both cases, the $\alpha$-form and the $\beta$-form can be purified to a level of 95% or greater purity. Also described herein are methods for producing the $\alpha$-form or the $\beta$-form at purities of 98% or greater.

Also provided herein are methods for the separation and purification of analogues of $\alpha$- and $\beta$-PGG in which the glucose part of the PGG is substituted by other sugars such as other hexoses, pentoses, or tetroses, in which the ring oxygen of the sugar analogue is substituted by carbon, nitrogen, or sulfur. With respect to these sugars, the methods described herein are able to separate $\alpha$-PGG analogues and $\beta$-PGG analogues. This method of separation is further enhanced: when there is more than 50% of the $\alpha$-PGG analogue or more than 50% of the $\beta$-PGG analogue present, respectively, in the impure starting material. In accordance with the methods described herein, both the $\alpha$-PGG analogues and the $\beta$-PGG analogues can be purified to purities of 95% or greater. Also provided are methods for producing the $\alpha$-form or the $\beta$-form at purities of 98% or greater.

Also provided are methods of separation and purification of analogues of $\alpha$- and $\beta$-PGG wherein the gallic acid part of the PGG is replaced by other phenols. In some embodiments, the phenols include, but are not limited to 2,3-dihydroxybenzoic acid, 3,4-dihydroxybenzoic acid, and 3,5-dihydroxybenzoic acid. In accordance with the methods described herein, these $\alpha$-PGG analogues and $\beta$-PGG analogues may be separated from mixtures of $\alpha$-PGG analogues and $\beta$-PGG analogues. In some embodiments, the starting material for the purification of the $\alpha$-form of the analogues contains more than 50% of the $\alpha$-form, and the staring material for the purified $\beta$-form of the analogue contains more than 50% of the $\beta$-form. Additionally, both the $\alpha$-PGG analogues and $\beta$-PGG analogues having the gallic acid replaced by another phenol may be purified to 95% or greater purity, or 98% or greater purity.

The method for separation of $\alpha$-PGG from a mixture of $\alpha$-PGG and $\beta$-PGG comprises the steps of (a) adding water to a sample containing 50% or more $\alpha$-PGG and 50% or less $\beta$-PGG; (b) mixing the PGG and water to dissolve the PGG; (c) filtering out any undissolved particles; and (d) allowing the filtered solution to stand undisturbed until crystals form. In some embodiments, the water used is double distilled water. In some embodiments, the ratio of water to PGG is about 20 mL of water for about 1 g of PGG. In some embodiments, the mixing in step is done for about 5 minutes. Optionally, the mixing step may be done at an elevated temperature, to aid in dissolution of the PGG. In some embodiments, the mixing step is carried out at 80° C., by placing the flask in a water bath incubator, or similar. In some embodiments, the filtration is done through a 45µ filter. In some embodiments, the flask contained the filtered solution is allowed to stand at room temperature, however, the flask may be kept at a lower temperature to speed up formation of the crystals. The method may be repeated to obtain purer $\alpha$-PGG. In accordance with the methods described herein, this method for purification of $\alpha$-PGG may also be used for analogues of $\alpha$-PGG, including, but not limited to analogues in which the glucose of the PGG is substituted by a hexose, pentose, or tetrose; analogues in which the glucose is substituted by sugar analogues in which the ring oxygen is substituted by carbon, nitrogen, or sulfur; and analogues in which the gallic acid portion of the PGG is substituted by other phenols.

The method for separation of β-PGG from a mixture of α-PGG and β-PGG comprises the steps of (a) adding acetone to a sample containing 50% or more β-PGG and 50% or less α-PGG; (b) mixing the PGG and acetone to dissolve the PGG; (c) filtering out any undissolved particles; and (d) allowing the filtered solution to stand undisturbed until crystals form. In some embodiments, the acetone is added to the PGG at a ratio of about 5 mL acetone for about 1 g PGG. In some embodiments, the mixing in step (b) is done for about 5 minutes. Optionally, the mixing step (b) may be done at an elevated temperature, to aid in dissolution of the PGG. In some embodiments, step (b) is carried out at 80° C., by placing the flask in a water bath incubator, or similar. In some embodiments, the filtration is done through filter paper. In some embodiments, the flask contained the filtered solution is allowed to stand at room temperature, however, the flask may be kept at a lower temperature to speed up formation of the crystals in accordance with the method described herein, this method for purification of β-PGG may also be used for analogues of β-PGG, including, but not limited to analogues in which the glucose of the PGG is substituted by a hexose, pentose, or tetrose; analogues in which the glucose is substituted by sugar analogues in which the ring oxygen is substituted by carbon, nitrogen, or sulfur; and analogues in which the gallic acid portion of the PGG is substituted by other phenols.

The method for preparing single crystal α-PGG comprises the steps of (a) adding water to a sample of pure (95% or greater) α-PGG; (b) mixing the α-PGG and water to dissolve the α-PGG; (c) filtering out any undissolved particles, placing the filtered solution in a clean vessel; and (d) maintaining the filtered solution undisturbed until crystals appear. In some embodiments, double distilled water is used in the method of preparing a single crystal of α-PGG. In some embodiments, the water is added to the α-PGG at a ratio of about 100 mL of water for about 1.0 g α-PGG In some embodiments, the mixing in step (b) is done for about 5 minutes. Optionally, the solution may be heated during mixing step (b) to aid in dissolution of the α-PGG. In some embodiments, mixing step (b) is carried out at 80° C. In some embodiments, solution is filtered through filter paper in step (c). In some embodiments, step (d) is carried out at room temperature, for about 15 days. In accordance with the method described herein, this method for preparing single crystals of α-PGG may also be used for analogues of α-PGG, including, but not limited to analogues in which the glucose of the PGG is substituted by a hexose, pentose, or tetrose; analogues in which the glucose is substituted by sugar analogues in which the ring oxygen is substituted by carbon, nitrogen, or sulfur; and analogues in which the gallic acid portion of the PGG is substituted by other phenols.

The method for preparing single crystal β-PGG comprises the steps of (a) adding acetone to a sample of pure (95% or greater) β-PGG; (b) mixing the β-PGG and acetone to dissolve the β-PGG; (c) filtering out any undissolved particles, placing the filtered solution in a clean vessel; and (d) maintaining the filtered solution undisturbed until crystals appear. In some embodiments, the ratio of acetone to PGG is about 50 mL of acetone per about 1.0 g β-PGG. In some embodiments, the mixing in step (b) is done for about 5 minutes. Optionally, the solution may be heated during mixing step (b) to aid in dissolution of the PGG. In some embodiments, mixing step (b) is carried out at 80° C. In some embodiments, solution is filtered through filter paper in step (c). In some embodiments, step (d) is carried out at room temperature for about 20 days.

This method for preparing single crystals of β-PGG may also be used for analogues of β-PGG, including, but not limited to analogues in which the glucose of the PGG is substituted by a hexose, pentose, or tetrose; analogues in which the glucose is substituted by sugar analogues in which the ring oxygen is substituted by carbon, nitrogen, or sulfur; and analogues in which the gallic acid portion of the PGG is substituted by other phenols.

BRIEF DESCRIPTION OF THE FIGS.

FIG. 1 shows the crystal structures of α-PGG (left) and β-PGG (right) under differential interference contrast microscope.

DETAILED DESCRIPTION OF THE INVENTION

Provided herein are methods for separation and purification of the α- and β-isomers of PGG by crystallization. The methods described herein may also be used to separate the α- and β-isomers of many different PGG analogues, include some that are potentially useful as pharmaceutical agents. The methods described herein may be used for quantities ranging from laboratory scale to kilogram quantities, up to ton quantities, while still producing isomers with purities of 95% or greater. Additionally, the methods described herein are very cost effective and environmentally friendly since water is the only solvent needed. The methods described herein may also be used to produce single crystals of α-PGG, β-PGG or analogues thereof.

Since the methods described herein achieve separation and purification α- and β-PGG and analogues thereof on a kilogram to ton scale, the methods are suitable for industrial application. Furthermore, the methods described herein are inexpensive—the only solvent needed is water, and standard instrumentation can be used with the inventive methods. In addition, the process is performed at room temperature, which makes expensive and time-consuming heating and/or cooling steps unnecessary. The method is also environmentally friendly since no organic solvents are necessary, and the process can be run without heating and cooling.

Until now, the only method available to produce high purity α-PGG and β-PGG isomers was high performance liquid chromatography (HPLC). HPLC has many disadvantages, making it unsuitable for separation of large quantities of material. HPLC can only be used for the separation of milligram to gram-size quantities of PGG. In addition, it is slower and far more expensive than crystallization, requiring a complicated HPLC system that costs at least $25,000 to $30,000 to purchase. Furthermore, large quantities of solvent must be used to run the HPLC and significant amounts of compound must be sacrificed (discarded) to maintain high purity, resulting in a low yield of recovered material.

Using the methods described herein, PGG and its analogues may be separated and purified in water or water-based solvent systems, efficiently with very low cost and high yield. The methods described herein reduce the total cost to manufacture isomers of PGG and its analogues, at a purity of at least 95%, by more than 95%.

The methods described herein are useful for separating α-PGG from a mixture containing α-PGG and β-PGG and for separating β-PGG from a mixture containing both α-PGG and β-PGG. The methods of the present are especially suitable for separating α-PGG from a mixture of α-PGG and β-PGG that contains more than 50% α-PGG, as well as separating β-PGG from a mixture of α-PGG and β-PGG that contains more than 50% β-PGG.

The crystallization methods described herein provide α-PGG and β-PGG, and analogues thereof with purities of greater than 95%. In another embodiment, the methods described herein produce α-PGG or β-PGG, or analogues thereof, with purities of 98% or greater. Also provided are methods of growing single crystals of α-PGG and single crystals of β-PGG.

Also provided are methods for the separation and purification of analogues of many analogues of α- and β-PGG. In one such analogue, the glucose part of the PGG is substituted by other sugars, such as hexoses, pentoses, or tetroses. Hexoses that may be used include, but are not limited to galactose, mannose, idose, talose, altrose, allose, gulose, fructose, or similar. Pentoses that may be used include, but are not limited to xylose, ribose, arabinose, and lyxose. Tetroses that may be used include, but are not limited to threose and erythrose. The methods described herein are able to separate the α- and β-PGG analogues from mixtures of α and β, including the case where there is more than 50% of the α-form present and the case when there is more than 50% β-form present. In both cases, the α-form and the β-form can be purified to a level of 95% or greater purity.

A second class of PGG-analogues suitable for the separation and purification methods described herein are analogues of α- and β-PGG in which the glucose part of the PGG is substituted by sugar analogues, of glucose, other hexoses, pentoses, or tetroses, in which the ring oxygen of the sugar analogue is substituted by carbon, nitrogen, or sulfur. With respect to these analogues, the methods described herein are able to separate α-PGG analogues and β-PGG analogues. The methods are suitable for mixtures where there is more than 50% of the α-PGG analogue or more than 50% of the β-PGG analogue. In accordance with the methods described herein, both the α-PGG analogues and the β-PGG analogues can be purified to purities of 95% or greater.

Also provided are methods of separation and purification of analogues of α- and β-PGG wherein the gallic acid part of the PGG is replaced by other phenols. Other phenols that may be used include, but are not limited to 2,3-dihydroxybenzoic acid, 3,4-dihydroxybenzoic acid, and 3,5-dihydroxybenzoic acid. In accordance with the methods described herein, these α-PGG analogues and β-PGG analogues may be separated from mixtures of α-PGG analogues and β-PGG analogues containing either more than 50% of the α-form or mixtures containing more than 50% of the β-form. Additionally, both the α-PGG analogues and β-PGG analogues having the gallic acid replaced by another phenol may be purified to 95% or greater purity.

Methods

Standard Operation Procedure of Crystallization of α-PGG or its Analogues

Crystallization is carried out on a laboratory scale as follows: (1) 1.0 g of a sample containing α-PGG having a purity of 50% or more is added to a 100-mL flask. (2) 20 mL of double distilled water is then added to the flask. (3) The flask is placed in an 80° C. water bath incubator for about 5 minutes, and gently shaken to dissolve the sample. (4) Any undissolved particles are removed using a 0.45 μm filter membrane. The filtered solution is added to a clean flask. (5) The flask is kept undisturbed at room temperature for approximately 5-7 days, until some white crystals appear.

The speed of crystallization is affected by temperature, and crystallization may be accelerated by keeping the flask at a temperature below room temperature.

If higher purity is desired, filter the crystals and repeat steps 1-5. A sample with purity higher than 98% may be obtained by repeating these steps more than four times.

To scale up the procedure, add 20 mL of double distilled water for every 1 g of sample and follow the procedure as outlined above.

Standard Operation Procedure for Growing Single Crystals of α-PGG (1) Add 1.0 g of 95% or greater purity α-PGG to a 200 mL flask. (2) Add 100 mL double distilled water to the flask. (3) Put the flask in an 80° C. water bath incubator for about 5 minutes, gently shake the flask to dissolve the sample. (4) Remove any undissolved particles with filter paper, adding the clear, filtered solution to a clean flask. (5) Leave the flask undisturbed, at room temperature, for about 15 days, until some thin, colorless, needle crystals appear. (6) Filter the crystals and store them in a sealed flask.

Standard Operation Procedure for Crystallization of β-PGG

The procedure for crystallization of β-PGG is as follows: (1) Add 1.0 g of sample contain β-PGG, having 50% or greater purity, into a 10 mL flask. (2) Add 5.0-mL of acetone to the flask. (3) Place the flask hi an 80° C. water bath incubator for approximately 10 minutes, gently shake the flask to dissolve the sample. (4) Filter the solution through filter paper, adding the filtered solution to a clean flask. (5) Leave the flask undisturbed at room temperature for about 15 days, until some colorless needle crystals appear. (6) Filter the crystals and repeat steps 1-5 if higher purity is desired. For scaling up the procedure, add acetone in the proportion of 1 g sample to 5 g acetone and crystallize the β-PGG.

Standard Operation Procedure for Growing Single Crystals of β-PGG (1) Add 1.0 g sample containing pure (95% or greater) β-PGG to a 100 mL flask. (2) Add 50 mL of acetone to the flask. (3) Place the flask in an 80° C. water bath incubator for about 10 minutes, gently shaking the flask to dissolve the sample. (4) Filter the solution through filter paper, adding the filtered solution to a clear flask. (5) Leave the flask undisturbed at room temperature for about 26 days, until some colorless needle crystals appear. (6) Filter the crystals and store the crystals in a sealed flask.

The invention claimed is:

1. A method for separation of α-penta-O-galloyl-D-glucose (PGG) from a mixture of α-PGG and β-PGG comprising the steps of:
   a) adding water to a PGG mixture containing 50% or more α-PGG and 50% or less β-PGG;
   b) mixing the PGG and water to dissolve the PGG;
   c) filtering out any undissolved particles; and
   allowing the filtered solution to stand undisturbed until crystals form
wherein the crystals comprise the α-PGG.

2. The method of claim 1 wherein double distilled water is used in step (a).

3. The method of claim 1 wherein the water to PGG ratio is about 20 mL of water for about 1 g of PGG.

4. The method of claim 1 wherein the mixing step is done for about 5 minutes.

5. The method of claim 1 wherein the mixing step is done at a temperature greater than 20° C.

6. The method of claim 5 wherein the mixing step is done at 80° C.

7. The method of claim 1 wherein the filtering step is done using a 45 μm filter.

8. The method of claim 1 wherein the filtered solution of step (d) is allowed to stand at a temperature lower than 20° C.

9. The method of claim 1 wherein the purity of the α-PGG is 95% or greater.

10. A method for separation of β-PGG from a mixture of α-PGG and β-PGG comprising the steps of
 a) adding acetone to a mixture of PGG containing 50% or more β-PGG and 50% or less α-PGG;
 b) mixing the PGG and acetone to dissolve the PGG;
 c) filtering out any undissolved particles; and
 d) allowing the filtered solution to stand undisturbed until crystals form
wherein the crystals comprise the β-PGG.

11. The method of claim 10 wherein the acetone is added to the PGG at a ratio of about 5 mL acetone for about 1 g PGG.

12. The method of claim 10 wherein the mixing in mixing in step (b) is done for about 5 minutes.

13. The method of claim 10 wherein the mixing step (b) may be done at a temperature greater than 20° C.

14. The method of claim 13 wherein the mixing step (b) is carried out at 80° C.

15. The method of claim 10 wherein the filtering step is done through filter paper.

16. The method of claim 10 wherein step (d) is done at a temperature lower than 20° C.

17. The method of claim 10 wherein the purity of the α-PGG is 95% or greater.

18. A method for preparing single crystal α-PGG comprising the steps of:
 a) adding water to a sample of α-PGG having a purity of 95% or greater;
 b) mixing the α-PGG and water to dissolve the α-PGG;
 c) filtering out any undissolved particles and placing the filtered solution in a clean vessel; and
 d) maintaining the filtered solution undisturbed until α-PGG crystals appear.

19. The method of claim 18 wherein the water is added to the α-PGG at a ratio of about 100 mL of water for about 1.0 g α-PGG.

20. The method of claim 18 wherein step (d) is carried out for about 15 days.

21. A method for preparing single crystal β-PGG comprising the steps of
 a) adding acetone to a sample of β-PGG having a purity of 95% or greater;
 b) mixing the β-PGG and acetone to dissolve the β-PGG;
 c) filtering out any undissolved particles, placing the filtered solution in a clean vessel; and
 d) maintaining the filtered solution undisturbed until crystals appear.

22. The method of claim 21 wherein ratio of acetone to PGG is about 50 mL of acetone per about 1.0 g β-PGG.

23. The method of claim 21 wherein step (d) is carried out for about 20 days.

* * * * *